US011400280B2

(12) United States Patent
Stone et al.

(10) Patent No.: US 11,400,280 B2
(45) Date of Patent: Aug. 2, 2022

(54) DEPLOYABLE ELECTRODE ARRAY LEAD ASSEMBLY FOR IMPLANTABLE ELECTRICAL STIMULATION

(71) Applicant: Medtronic, Inc., Minneapolis, MN (US)

(72) Inventors: Richard T. Stone, Minneapolis, MN (US); Michael T. Hegland, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 798 days.

(21) Appl. No.: 15/850,984

(22) Filed: Dec. 21, 2017

(65) Prior Publication Data
US 2018/0178001 A1     Jun. 28, 2018

Related U.S. Application Data

(60) Provisional application No. 62/437,863, filed on Dec. 22, 2016.

(51) Int. Cl.
*A61N 1/05* (2006.01)
*A61N 1/36* (2006.01)

(52) U.S. Cl.
CPC ......... *A61N 1/0534* (2013.01); *A61N 1/0536* (2013.01); *A61N 1/0558* (2013.01);
(Continued)

(58) Field of Classification Search
None
See application file for complete search history.

(56) References Cited

U.S. PATENT DOCUMENTS 5,895,416 A    4/1999  Barreras, Sr. et al.
6,161,047 A   12/2000  Rossi
(Continued)

FOREIGN PATENT DOCUMENTS

EP        2862595 A1    4/2015
WO   WO 00/67656 A1   11/2000
(Continued)

OTHER PUBLICATIONS

International Search Report and Written Opinion, PCT/US2017/067930, dated Mar. 7, 2018, 12 pages.
(Continued)

*Primary Examiner* — Ankit D Tejani
(74) *Attorney, Agent, or Firm* — Mueting Raasch Group

(57) ABSTRACT

A lead assembly includes a central lead member having a distal portion configured to extend along a longitudinal axis. The lead assembly also includes two or more side lead members disposed around the central lead member. Each side lead member includes a deploying portion extending at an angle away from the longitudinal axis. Each deploying portion has a proximal portion and a distal portion. The distal portion is laterally spaced from the central lead member and extends more parallel to the longitudinal axis than the proximal portion. The lead assembly also includes one or more electrodes attached to the distal portion of the deploying portion of each side lead member. The lead assembly optionally includes a cannula comprising a lumen, an end portion, and a buckler disposed in the lumen on the end portion for deploying the lead members.

20 Claims, 11 Drawing Sheets

(52) U.S. Cl.
CPC ..... *A61N 1/36062* (2017.08); *A61N 1/36067* (2013.01); *A61N 1/36017* (2013.01); *A61N 1/36128* (2013.01)

(56) References Cited

U.S. PATENT DOCUMENTS

| | | |
|---|---|---|
| 7,181,288 B1 | 2/2007 | Rezai et al. |
| 2002/0062143 A1 | 5/2002 | Baudino et al. |
| 2006/0161235 A1 | 7/2006 | King |
| 2010/0114283 A1 | 5/2010 | King |
| 2010/0137926 A1 | 6/2010 | King et al. |
| 2010/0241179 A1 | 9/2010 | Gielen et al. |
| 2010/0268298 A1 | 10/2010 | Moffitt et al. |
| 2012/0083866 A1 | 4/2012 | King et al. |
| 2016/0023005 A1* | 1/2016 | Perryman .......... A61N 1/37229 607/60 |

FOREIGN PATENT DOCUMENTS

| | | |
|---|---|---|
| WO | WO 2008/068759 A2 | 6/2008 |
| WO | WO 2011/121089 A1 | 10/2011 |

OTHER PUBLICATIONS

International Preliminary Report on Patentability, PCT/US2017/067930, dated Jul. 4, 2019, 7 pages.

\* cited by examiner

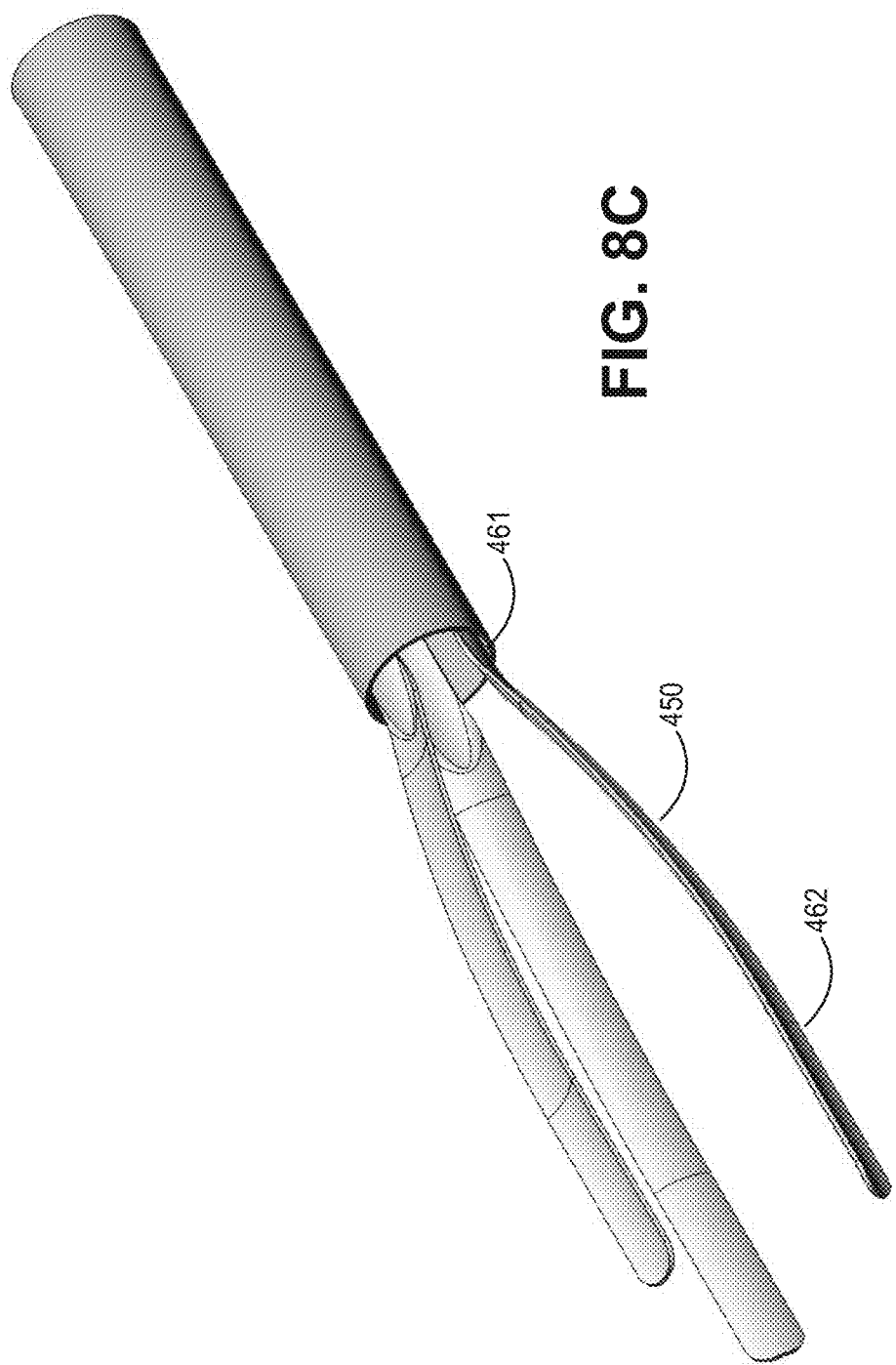

DEPLOYABLE ELECTRODE ARRAY LEAD ASSEMBLY FOR IMPLANTABLE ELECTRICAL STIMULATION

TECHNICAL FIELD

The present disclosure relates to a lead assembly for electrical stimulation. In particular, the present disclosure relates to a lead assembly configured to deploy lead members along a constant-radius arc to form an implanted electrode array for deep brain stimulation.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. In some cases, implantable electrodes may be coupled to an external electrical stimulation generator via one or more fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

In the case of deep brain stimulation (DBS), the stimulation treatment requires stimulation of a volume of neural tissue. Since the exact location of the desired tissue may be unknown and coupled with targeting errors, the capability to steer an electrical field in two or three dimensions once a lead is implanted is very desirable. Changing the electric field distribution changes the distribution of neurons recruited during a stimulus output thus providing a user the capability to alter the physiological response to the stimulation. The steerability of the electric field allows the user to selectively activate different groups of nerve cells without physically moving the electrodes, which may increase risks associated with damaging brain tissue and associated tissue known to those in the art.

Without sufficient field steering capabilities, however, a patient undergoing some DBS implantation procedures may need to remain conscious during the implantation procedure to confirm brain structure location, such as the subthalamic nucleus (e.g., a "closed loop implant" procedure). In some procedures, general anesthesia cannot be used on the patient while performing microelectrode recording, because general anesthesia may disrupt normal brain signals known to those in the art.

Field steering is often limited by the geometry of the leads. For example, a single DBS lead with one or more segmented-electrodes can allow for limited lateral field steering (e.g., less than about 1 mm of lateral field steering when using a 1.3 mm diameter lead). Adding additional electrodes lateral to the anatomical target may be effected by using a deployable lead system. However, prior art deployable leads do not provide a system with greater lateral field steering that permits explantation of the deployable lead without the risk of simultaneously removing significant brain tissue along with the deployable lead, while still providing easy lead management for an implanting surgeon.

Accordingly, there remains a need in the art to provide a deployable lead with a simple, easy-to-visualize electrode array geometry that provides improved lateral field steering and a deployment configuration that facilitates both safe and easy lead implantation and lead explantation.

SUMMARY

According to one aspect of the present disclosure, a lead assembly includes a central lead member having a distal portion configured to extend along a longitudinal axis. The lead assembly also includes two or more side lead members disposed around the central lead member. Each side lead member includes a deploying portion extending at an angle away from the longitudinal axis. Each deploying portion has a proximal portion and a distal portion. The distal portion is laterally spaced from the central lead member and extends more parallel to the longitudinal axis than the proximal portion. The lead assembly also includes one or more electrodes attached to the distal portion of the deploying portion of each side lead member.

According to another aspect of the present disclosure, a lead assembly includes a cannula having a lumen, an end portion, and a buckler disposed in the lumen on the end portion. The lead assembly also includes a central lead member disposed within the lumen of the cannula. The lead assembly further includes two or more side lead members having a deploying portion with a proximal portion and a distal portion. The deploying portion is disposed about the central lead member within the lumen of the cannula and laterally constrained by the cannula. The distal portion of the deploying portion extends non-linearly when deployed out of the cannula. The lead assembly includes two or more electrodes attached to each of the central and side lead members.

It is to be understood that both the foregoing general description and the following detailed description present embodiments of the subject matter of the present disclosure, and are intended to provide an overview or framework for understanding the nature and character of the subject matter of the present disclosure as it is claimed.

BRIEF DESCRIPTION OF THE DRAWINGS

The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

FIG. 8C is a perspective view of the cannula and deployment stylets without the lead assembly.

Figure 1:
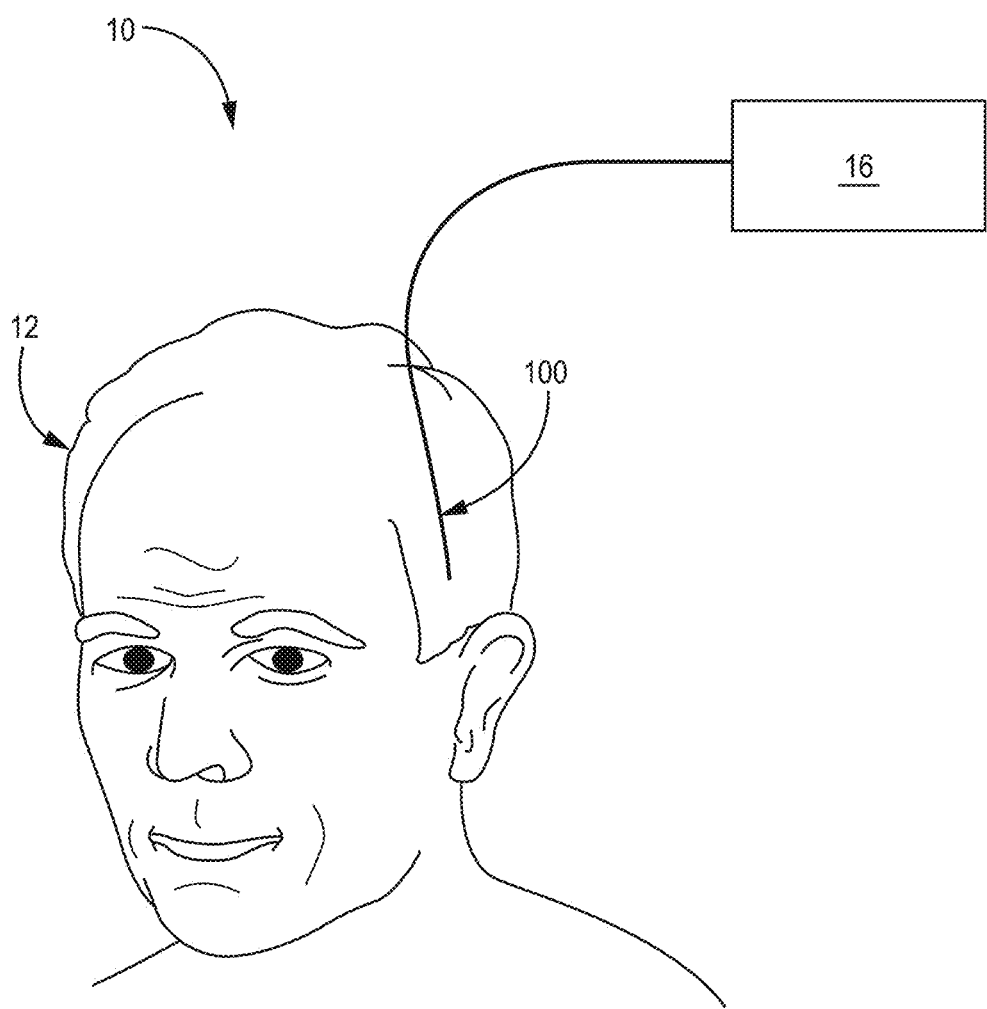
FIG. 1 is a schematic representation of a stimulation system including a lead assembly.

The disclosure may be more completely understood in consideration of the following detailed description of various embodiments of the disclosure in connection with the accompanying drawings.

DETAILED DESCRIPTION

The present disclosure describes a lead assembly having a central lead member extending along a longitudinal axis and two or more side lead members each with a distal portion laterally spaced from the central lead member when deployed. In the deployed configuration, the side members extend outward at a small angle from the end of the cannula and then turn toward the longitudinal axis (e.g., inwardly, generally to be more parallel to the longitudinal axis). The deployed side lead members can each have a deploying portion having proximal and distal portions. The proximal and distal portions may extend non-linearly away from the longitudinal axis. The distal portion may extend more parallel to the longitudinal axis than the proximal portion.

The deploying portion may extend along a non-linear pathway. The non-linear pathway may begin directed away from the longitudinal axis and curve inwardly toward a direction parallel to the longitudinal axis. The non-linear pathway may be described as convex. In some embodiments, the non-linear pathway is a constant radius pathway in the shape of an arc. A stylet may be coupled to each side lead member defining the non-linear pathway. The stylet may have an arcuate cross-section. The inwardly curved arc pathway of the side lead member when deployed from the cannula may facilitate the use of a simple deployment process for positioning electrodes in the brain tissue.

Electrodes may be attached to the distal portions of the lead members to define an electrode array with a simple geometry. The electrode array may include two or more rows of longitudinally-spaced electrodes. In another example, the electrode array need only include a single row. Each row may include an electrode from each of the lead members. The deploying portions of the side lead members may be non-linear and extend along an almost straight line. With the inward curve of each deploying portion of the side lead members, the distal portions of the deploying portions may be parallel or almost parallel to one another. In some embodiments, the spatial configuration of the electrodes in each row is the same or almost the same.

Before deployment, the lead members may be constrained within a cannula and exhibit a rounded cross-section. As the lead members are deployed out of the cannula, the side lead members may be directed by a buckler within the cannula. For example, the buckler may engage and buckle the stylet coupled to the side lead member, allowing the side lead member and the stylet to be directed away from the axis along the cannula.

A distal part of the buckler may define an exit angle away from the end of the cannula.

The defined exit angle may be a maximum angle for the side lead members. The maximum angle may be small while enabling sufficient lateral space between the electrodes on the lead members to facilitate sufficient lateral field steering that may mitigate or eliminate the need to reposition the electrodes. The patient may be generally anesthetized or unconscious during implantation, and stimulation therapy may be configured after implantation is complete (e.g., an "open loop implant" procedure). With the small exit angle from the end of the cannula, the side lead members may be removed from the brain of a patient without extracting significant brain tissue during the lead removal.

Reference will now be made to the drawings, which depict one or more aspects described in this disclosure. However, it will be understood that other aspects not depicted in the drawings fall within the scope and spirit of this disclosure. Like numbers used in the figures refer to like components, steps and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 shows a stimulation system 10 in schematic representation of a lead assembly 100. Although lead assembly 100 is shown, any lead assembly of the present disclosure may be used, such as lead assembly 200 (FIG. 4), lead assembly 300 (FIG. 6), and lead assembly 400 (FIG. 7), or any alternatives or combinations of features contemplated herein.

The lead assembly 100 may be guided by a physician and implanted into the head 12 of a patient. In some embodiments, the lead assembly 100 has a deployable position and a deployed position. As the lead assembly 100 is implanted, the lead assembly may be in a deployable position. The deployable position may have a minimal cross-sectional width or diameter, as well as a minimal cross-sectional area, so as to easily facilitate tunneling through brain tissue within a lead delivery cannula while mitigating potential damage to the brain tissue.

When the lead assembly 100 has reached position just above a potential stimulation site within the head 12 of the patient, the physician may initiate deployment of the lead assembly 100 into the deployed position. In the deployed position, the electrodes of the lead assembly 100 may extend laterally. In particular, the electrodes of the lead assembly 100 may extend laterally farther than about a diameter of a single lead so as to facilitate a much wider range of lateral electric field steering for stimulating brain tissue than the capability of other leads, for example, a segmented electrode lead, which cannot steer laterally no farther than the diameter of a single lead.

Once deployed, the lead assembly 100 or lead members 102 may also be explanted or extracted from the patient. In some embodiments, the cannula 108 may be extracted before or with the extraction of the lead members 102.

As one end of the lead assembly 100 is implanted, the other end may be connected to a stimulation device 16 configured to provide electrical stimulation for configuring or delivering stimulation therapy. The stimulation device 16 may include a controller configured to steer an electric field for stimulation through electrodes on the lead assembly 100 when deployed. The stimulation device 16 may also include a hermetic multiplexer coupled between the electrodes and the controller. As shown, stimulation device 16 is external to the patient. However, the simulation device 16 may also be implanted within the patient. Two examples of locations within the patient would be on or into the skull or a pectoral implant just below the clavicle.

In some embodiments, the stimulation device 16 may include a processor, memory, stimulation generator, sensing module, switch module, telemetry module, and power source. Memory, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory may store computer-readable instructions that, when executed by processor, cause implantable medical device (IMD) to perform various functions described herein.

Memory can store therapy programs and operating instructions, e.g., in separate memories within memory or separate areas within memory. Each stored therapy program defines a particular program of therapy in terms of respective values for electrical stimulation parameters, such as an electrode combination, current or voltage amplitude, and, if stimulation generator generates and delivers stimulation pulses, the therapy programs may define values for a pulse width, and pulse rate of a stimulation signal. The stimulation signals delivered by the IMD may be of any form, such as charge balanced stimulation pulses, continuous-wave signals (e.g., sine waves), or the like. Operating instructions guide general operation of the IMD under control of processor, and may include instructions for monitoring brain signals within one or more brain regions via electrodes and delivering electrical stimulation therapy to patient.

The stimulation generator, under the control of the processor, generates stimulation signals for delivery to patient via selected combinations of electrodes. In some examples, the stimulation generator generates and delivers stimulation signals to one or more target regions of brain, via a select combination of electrodes, based on one or more stored therapy programs. The target tissue sites within the brain for stimulation signals or other types of therapy and stimulation parameter values may depend on the patient condition for which therapy system is implemented to manage.

The processors described in this disclosure, including the processor, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. The processor is configured to the control stimulation generator according to therapy programs stored by memory to apply particular stimulation parameter values specified by one or more therapy programs.

Processor may control the switch module to apply the stimulation signals generated by the stimulation generator to selected combinations of electrodes. In particular, the switch module may couple stimulation signals to selected conductors within leads, which, in turn, deliver the stimulation signals to selected electrodes. The Switch module may be a switch array, switch matrix, multiplexer, or any other type of switching module configured to selectively couple stimulation energy to selected electrodes and to selectively sense bioelectrical brain signals from selected electrodes. Hence, the stimulation generator is coupled to electrodes via the switch module and conductors within leads. In some examples, however, the stimulation device 16 does not include the switch module. For example, the stimulation device 16 may include multiple sources of stimulation energy (e.g., current sources).

The stimulation generator may be a single channel or multi-channel stimulation generator. In particular, the stimulation generator may be capable of delivering a single stimulation pulse, multiple stimulation pulses or continuous signal at a given time via a single electrode combination or multiple stimulation pulses at a given time via multiple electrode combinations. In some examples, however, the stimulation generator and switch module may be configured to deliver multiple channels on a time-interleaved basis. For example, the switch module may serve to time divide the output of stimulation generator across different electrode combinations at different times to deliver multiple programs or channels of stimulation energy to patient.

The sensing module, under the control of the processor, is configured to sense bioelectrical brain signals of the patient via a selected subset of electrodes or with one or more electrodes and at least a portion of a conductive outer housing of the stimulation device 16, an electrode on the outer housing of the stimulation device 16 or another reference. The processor may control the switch module to electrically connect the sensing module to selected electrodes. In this way, the sensing module may selectively sense bioelectrical brain signals with different combinations of electrodes (and/or a reference other than an electrode).

Although the sensing module is incorporated into a common housing with the stimulation generator and the processor, in other examples, the sensing module is in a separate outer housing from the outer housing of the stimulation device 16 and communicates with the processor via wired or wireless communication techniques.

The telemetry module is configured to support wireless communication between the stimulation device 16 and an external programmer or another computing device under the control of the processor. The processor of the stimulation device 16 may receive, as updates to programs, values for various stimulation parameters from the programmer via the telemetry module. The updates to the therapy programs may be stored within the therapy programs portion of memory. The telemetry module in the stimulation device 16, as well as telemetry modules in other devices and systems described herein, such as the programmer, may accomplish communication by RF communication techniques. In addition, the telemetry module may communicate with the external medical device programmer via proximal inductive interaction of the stimulation device 16 with the programmer. Accordingly, the telemetry module may send information to the external programmer on a continuous basis, at periodic intervals, or upon request from the stimulation device 16 or the programmer.

The power source delivers operating power to various components of the stimulation device 16. The power source may include a small rechargeable or non-rechargeable battery and a power generation circuit to produce the operating power. Recharging may be accomplished through proximal inductive interaction between an external charger and an inductive charging coil within the stimulation device 16. In some examples, power requirements may be small enough to allow the stimulation device 16 to utilize patient motion and implement a kinetic energy-scavenging device to trickle charge a rechargeable battery. In other examples, traditional batteries may be used for a limited period of time.

Figures 2A, 2B, 2C:
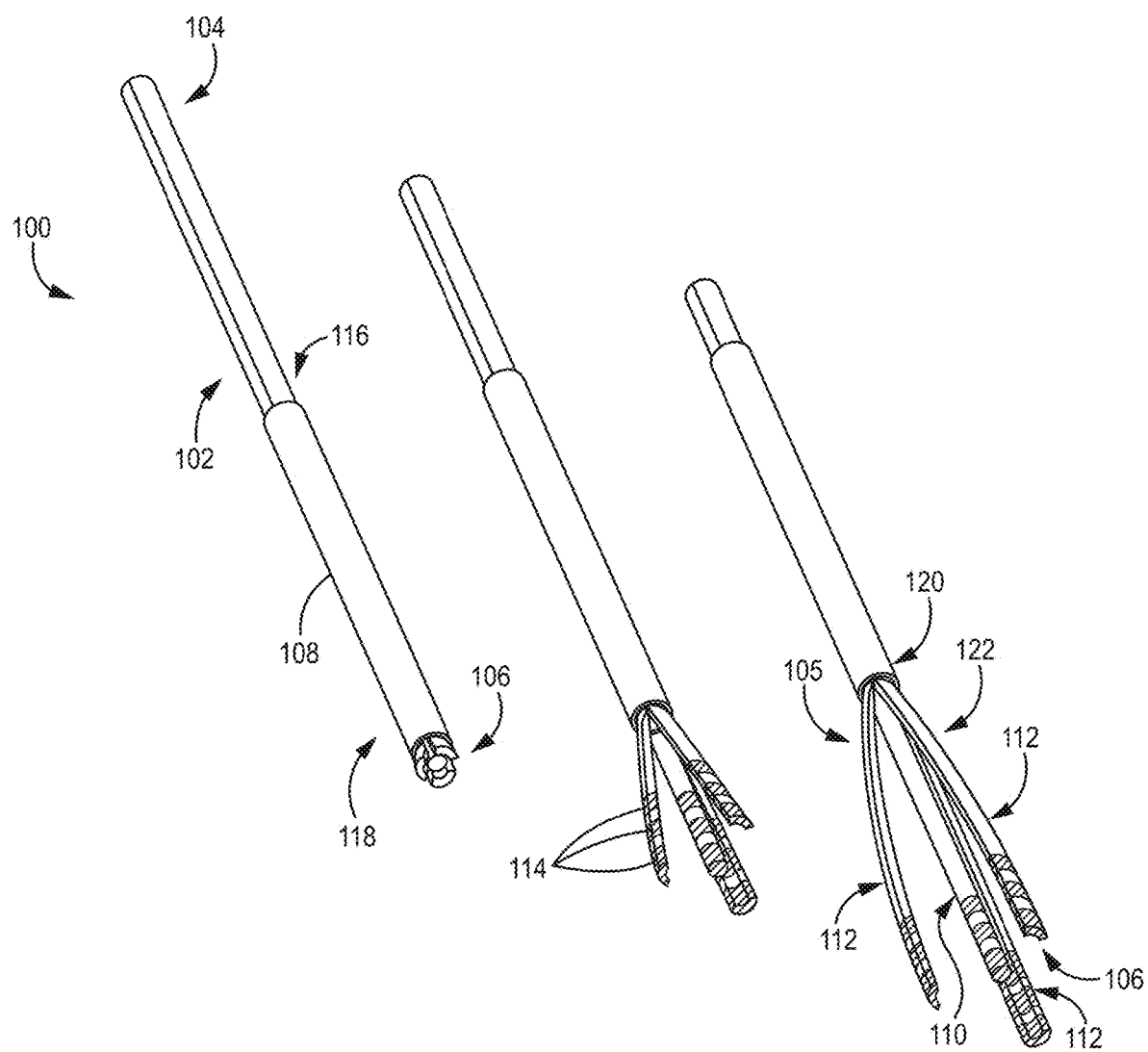
FIGS. 2A-C are perspective views of the lead assembly of FIG. 1 shown in various positions.

FIGS. 2A-C show the lead assembly 100 in various positions throughout a deployment process. In FIG. 2A, the lead assembly 100 is shown in a deployable position or almost deployable position (e.g., retracted). The lead assembly 100 may be implanted while in the deployable position. In FIG. 2C, the lead assembly 100 is shown in a deployed position or almost deployed position (e.g., protracted). When the lead assembly 100 reaches an implantation site, the lead assembly may be moved into the deployed position to form the electrode array for stimulation. FIG. 2B shows an intermediate position of the lead assembly 100, between the deployable and deployed positions.

The lead assembly 100 may include lead members 102 (e.g., leads) having a bundled portion 104 and a deploying portion 122 extending distally from the bundled portion. The lead members 102 may also include a distal portion 106. The distal portion 106 may form a part of the deploying portion 122. The lead assembly 100 extends through a lumen 116 of the cannula 108. The lead members 102 may deploy out of the lumen 116 through an end portion 118 of the cannula 108. The end portion 118 may be a distal end portion of the cannula 108. The cannula 108 may include one or more features that interact with the lead members 102 during the deployment process, such as a buckler 440 described herein in more detail (see FIG. 7).

The lead members 102 may include a central lead member 110 and one or more side lead members 112. For example, the lead members 102 may include one, two, three, four, or more side lead members 112. In the illustrated embodiment, the lead members 102 include three side lead members 112. The lead members 102 may be disposed within the lumen 116 of the cannula 108 in the deployable position. The deploying portion 122 of the lead members 102 may not be disposed within the lumen 116 of the cannula 108 in the deployed position. For example, as shown in FIG. 2C, the bundled portion 104 of the lead members 102 are disposed within the lumen 116, whereas the deploying portion 122 of the lead members 102 are not disposed within the lumen 116, in the deployed position. The deploying portion 122 may include a proximal portion 105. Once deployed, the deploying portion 122 including the proximal portion 105 and the distal portion 106 may be extended from the cannula 108.

The side lead members 112 may be disposed around the central lead member 110. In the deployable position, the side lead members 112 may be laterally constrained by the cannula 108. The central lead member 110 and side lead members 112 may be generally linear or may conform to the shape of the lumen 116 of the cannula 108 in the deployable position.

The lead members 102 may define a round cross-section in the deployable position while constrained in the lumen 116 of the cannula 108. For example, the round cross-section may be circular, ovular, elliptical, ring-shaped, disk-shaped, or other rounded shape. In some embodiments, the central lead member 110 may define a circular cross-section, and each side lead member 112 may define an arcuate cross-section. In some embodiments, the lead members 102 may define a cross-sectional width or diameter that is less than or equal to about 7.6 mm (0.3 in.), about 5.1 mm (0.2 in.), about 2.5 mm (0.1 in.), about 1.3 mm (0.050 in.), or about 1 mm (0.040 in.). In general, the diameter of the lead members 102 is about the same as some conventional leads with only a single lead member.

The bundled portion 104 of the lead members 102 may define a round cross-section, even after deployment. The bundled portion 104 may not split like the deploying portion 122 does during deployment out of the cannula 108. In some embodiments, one or more of the lead members 102 in the bundled portion 104 may be integrally formed, for example, to form a single lead body.

The central lead member 110 may extend linearly when unconstrained in the deployed position. In comparison, portions of the side lead members 112 may extend non-linearly when unconstrained by the cannula 108 in the deployed position. In some embodiments, the bundled portion 104 of each side lead member 112 extends linearly in the deployed position, while a deploying portion 122 of the side lead member 112 extending distally from a buckling point 120 extends nonlinearly when unconstrained by the cannula 108.

In some embodiments, the deploying portion 122 of the lead members 102 extending out of the cannula 108 has a length in a range from about 1 cm to about 4 cm, about 1.5 cm to about 3.5 cm, or equal to about 3 cm.

The side lead members 112 may extend along a non-linear pathway when deployed from the cannula 108. In particular, the deploying portion 122 may extend along the non-linear pathway. The non-linear pathway may be a constant-curvature pathway. Each side lead member 112 may include or be coupled to a structure to define the non-linear pathway, such as stylet 450 described herein in more detail (see FIGS. 8A-E). In some embodiments, the deploying portion 122 of the side lead members 112 extend along a constant-radius arc 201 (see FIG. 4). When each side lead member 112 extends along a constant-radius arc, each side lead member 112 can protract and retract along a single pathway. A side lead member 112 that can be implanted and extracted along a single pathway may provide a simple geometric configuration for deploying an array of electrodes in the brain tissue. In some embodiments, the constant-radius arc is defined by a radius in a range from about a 12.7 cm (5 in.) to about 25.4 cm (10 in.), about 15.2 cm (6 in.) to about 20.3 cm (8 in.), or about a 17.8 cm (7 in.) to about a 25.4 cm (10 in.).

The central lead member 110 may also protract and retract along a single pathway. In some embodiments, the central lead member 110 extends linearly. The central lead member 110 may be described as having a constant-radius arc with an infinite radius, defining a linear pathway for implantation and extraction.

The lead assembly 100 may include one or more electrodes 114 attached to the lead members 102. In some embodiments, one, two, three, or more electrodes 114 are attached to each of the lead members 102. As shown, each of the lead members 102 has the same number of electrodes 114. However, in other embodiments (not shown), the lead members 102 do not have the same number of electrodes 114. When the lead assembly 100 is in the deployed position, the electrodes 114 may form an electrode array.

Each electrode 114 can be attached to the distal portion 106 of a lead member 102. The electrode 114 can be disposed anywhere on the distal portion 106. In some embodiments, the electrode 114 may surround the lead member 102, forming a ring around the lead member 102. In some embodiments, the electrode 114 may be disposed laterally on the outside or inside of a side lead member 112. In some embodiments, the electrode 114 may be formed of two or more electrode segments. For example, electrode 114 may include an inner and outer electrode pair. The side lead may partially shield the inner electrode from stimulating tissue outwardly and may partially shield the outer electrode from stimulating tissue inwardly. While more complicated than a single electrode, including two or more electrode segments may improve the ability to steer or shape the electrical field.

In some examples, one or more electrodes 114 may be attached to the proximal portion 105 and/or bundled portion 104 in addition to the electrodes 114 located at the distal portion 106.

The lead assembly 100 may include one or more filars (not shown) attached to one or more of the electrodes 114. In some embodiments, each electrode 114 is attached to one or more filars. The filars may electrically connect the electrodes 114 to the stimulation device 16 (FIG. 1). Each filar may be embedded within a lead member 102.

Figures 3A, 3B, 3C:
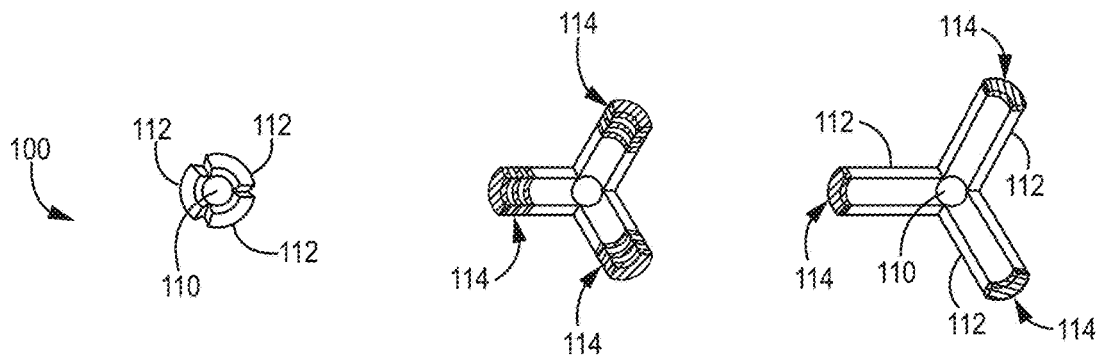
FIGS. 3A-C are end views of the lead assembly of FIG. 1, which correspond to the various positions shown in FIGS. 2A-C.

FIGS. 3A-C show end views of the lead assembly 100 in the same positions corresponding to FIGS. 2A-C. In the illustrated embodiment, as the lead assembly 100 is deployed longitudinally, the lead assembly also extends or expands laterally. As illustrated, the side lead members 112 are most extended in a deployed position (see FIG. 3C) and least extended in the deployable position (see FIG. 3A). The lateral space between the electrodes 114 also increases in distance as the lead assembly 100 is deployed.

Figure 4:
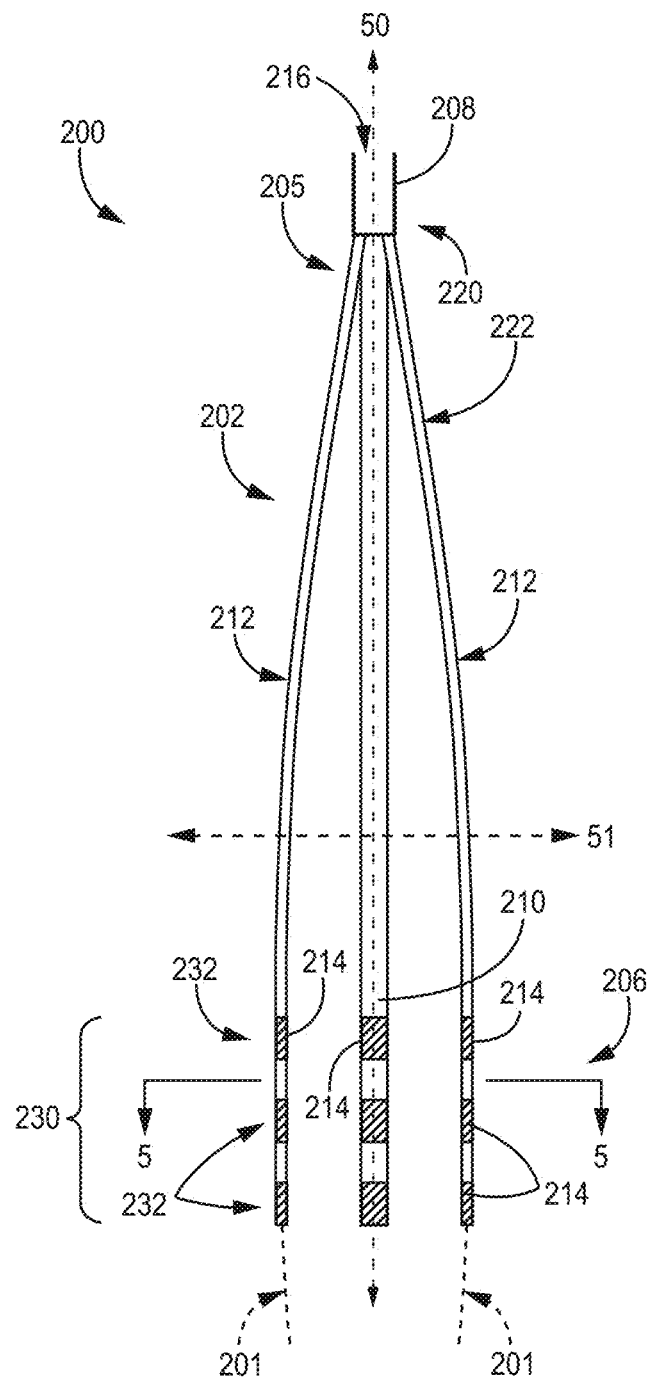
FIG. 4 is an elevation view of a lead assembly in a deployed position.

FIG. 4 shows an elevation view of lead members 202 of a lead assembly 200 in a deployed position. Many of the parts and components depicted in FIG. 4 are the same or similar to those depicted in and described with regard to FIG. 2. Reference is made to the discussion above regarding FIG. 2 for numbered elements depicted in but not specifically discussed with regard to FIG. 4. The lead assembly 200 is similar to lead assembly 100, and similar elements are numbered similarly (e.g., side lead member 112 is similar to side lead member 212). However, in the illustrated embodiment, the lead assembly 200 has four side lead members 212 (only two shown, plus a central lead member 210) as compared to the three side lead members 112 in the lead assembly 100 (FIG. 2).

The central lead member 210 can extend along a longitudinal axis 50. The distal portion 206 of each side lead member 212 is laterally spaced in a lateral plane 51 from the central lead member 210. In some embodiments, the side lead member 212 includes a proximal portion 205 of the deploying portion 222 extending out of the lumen 216 of the cannula 208 between a buckling point 220 and the distal portion 206 of the side lead member 212.

Along the deploying portion 222 of each side lead member 212, the lateral spacing increases extending longitudinally away from the cannula 208.

In the illustrated embodiment, the deploying portion 222 extends along a constant-radius arc 201 that curves toward a direction parallel to the longitudinal axis 50. As can be seen, if the distal portion 206 of the lead members 202 were to extend further along the arc 201, the distal portion 206 may begin to point toward the longitudinal axis 50.

The constant-radius arc may be described as convex. In some embodiments, when deployed or unconstrained by the cannula 208, the distal portion 206 of each side lead member 212 extends more parallel to the longitudinal axis 50 and the central lead member 210 than the proximal portion 205 of the deploying portion 222 of the side lead member 212. The convex arc of the side lead members 212 may allow the deploying portion 222 of each side lead member 212 to define the lateral extent of the electrode array 230 while the distal portion 206 of each side lead member 212 to be parallel or almost parallel (e.g., within about ±2 degrees or about ±1 degree) to the longitudinal axis 50 and the central lead member 210. In other words, the maximum angle of deflection away from the longitudinal axis 50 along the side lead member 212 may be immediately after or adjacent to the buckling point 220. The angle of deflection of the side lead member 212 may be less than the maximum at other points along the side lead member 212, such as the distal portion 206. In this manner, the constant-radius arc defined by the deploying portion 222 of the side lead member 212 may be convex when deployed or unconstrained. The convex shape may also be described in contrast to a concave shape, in which the side lead members 212 would flare laterally outwardly (e.g., less parallel to the longitudinal axis 50 or the central lead member 210).

One advantage of the convex shape is that the angle of the side lead member 212 away from the longitudinal axis 50 remains within a maximum angle. When the side lead member 212 is pulled, for example, to remove the side lead member 212, the risk of displacing or otherwise affecting brain tissue is reduced, particularly versus a concave shape or other shapes defining larger angles for the side lead member 212.

The electrodes 214 may define an electrode array 230. In some embodiments, the electrode array 230 is disposed on the distal portions 206 of the central lead member 210 and the side lead members 206. The electrodes 214 may define one, two, three, or more rows of electrodes 232. Each row of electrodes 232 may be longitudinally spaced from the other rows.

The lateral spacing between the side lead members 212 may define the lateral spacing of the electrode array 230. For various reasons, when a lead assembly 200 is being implanted, the placement of the electrodes 214 may be offset in the lateral direction from an ideal location. In some embodiments, the lateral distance between electrodes 214 may be set to mitigate the need to reposition the lead assembly 200 once deployed. In some embodiments, the lateral spacing between the electrodes 214 of the central lead member 210 and the electrodes 214 of the side lead members 212 is greater than or equal to about 1 mm, about 2 mm, about 3 mm, or about 4 mm. In some embodiments, the width or diameter of the electrode array 230 is greater than or equal to about 2 mm, about 4 mm, about 6 mm, or about 8 mm. In some embodiments, the width or diameter of the electrode array 230 is in a range from about 3 mm to about 10 mm or is equal to about 6 mm.

A controller connected to the electrode array 230 may be configured to steer the electrical field in the lateral direction from the central lead member 210 (e.g., longitudinal axis 50 at 0 mm) to a distance greater than or equal to about 1 mm, about 2 mm, about 3 mm, about 4 mm, or about 5 mm. In some embodiments, the electrical field can be steered in the lateral direction in a range from about 0 mm to about 4 mm or in a range from about 0 mm to about 2 mm.

The extent of lateral electrical field steering may correspond to the lateral spacing between the electrodes 214. In some embodiments, the diameter of the electrode array 230 is in a range from about 3 mm to about 10 mm and the extent of the lateral field steering is about 5 mm. In some embodiments, the diameter of the electrode array 230 is equal to about 6 mm and the extent of the lateral field steering is about 3 mm. Other combinations are also contemplated depending on the specific configuration of the stimulation system.

The electrode array 230 may have a simple geometric shape. A simple geometric shape may be more easily visualized by a user when configuring stimulation therapy. In some embodiments, the electrode array 230 is a uniform or almost uniform array. For example, the electrode array 230 may be formed of one or two rows or three rows 232 of electrodes 214 on the side lead members 212 and the central lead member 210.

Each row 232 of electrodes may have the same or almost the same spatial configuration.

In some embodiments, each electrode 214 on each lead member 202 may have a position relative to other electrodes 214 on other lead members 202 in one row 232, and the corresponding electrodes 214 have the same or almost the same position in other rows 232. In other words, the distance between the corresponding electrodes 214 from row-to-row may be the same or substantially the same (e.g., within about 10%, about 5%, or about 1% difference between distances). The distances between the electrodes 214 each row by each row may not be exactly uniform, for example, due to the non-linear curvature of the side lead members 212.

In the illustrated embodiment, the electrode array 230 includes electrodes 214 from at least two side lead members and the central lead member 210. Each row 232 includes an electrode 214 from each of the lead members 202. The distance between the electrode 214 on the central lead member 210 and each electrode 214 on the side lead members 212 is the same or almost the same in each row 232.

Figure 5A:
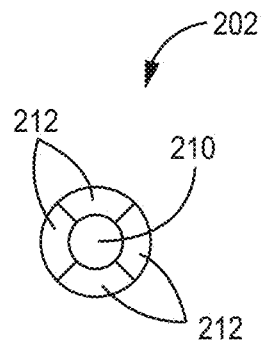
FIGS. 5A-B are schematic cross-sectional views of the lead assembly of FIG. 4 along line 5-5 in various positions.
Figure 5B:
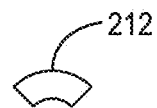
Figure 5B:
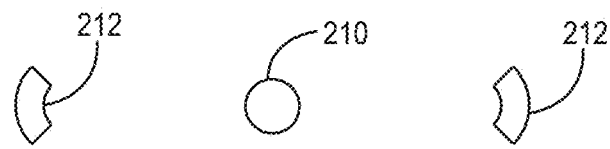
Figure 5B:

FIGS. 5A-B show schematic cross-sections of the lead members 202 along line 5-5 of FIG. 4 to further illustrate the expansion of the side lead members 212. FIG. 5A shows a cross-section of the lead members 202 in the deployable position. FIG. 5B shows a cross-section of the lead members 202 in the deployed position.

In some embodiments, the cross-section of the central lead member 210 is circular, and the cross-section of each side lead member 212 has an arcuate shape. For example, the arcuate shape may be described as the segment of a cylinder. The arcuate shape may allow the side lead members 212 to complement the shape of the central lead member 210 in the deployable position. The inner surfaces of the side lead members 212 may be completely or almost completely (e.g., at least about 75%, about 90%, about 95%, or about 99%) in contact with the outer surface of the central lead member 210. The complementary fit facilitated by the complementary shapes of the lead members 202 may facilitate a minimal cross-sectional area in the deployable position, which may facilitate minimal disruption to brain tissue during tunneling to implant the lead members 202. In some embodiments, the deployable cross-sectional width or diameter of the lead members 202 is less than or equal to about 2.5 mm (100 mils), about 1.9 mm (75 mils), about 1.3 mm (50 mils), or about 1 mm (40 mils). In some embodiments, the deployable cross-sectional width or diameter is in a range from about 0.6 mm (25 mils) to about 1.9 mm (75 mils), about 1.1 mm (45 mils) to about 1.4 mm (55 mils), or equal to about 1.3 mm (50 mils).

Once an implantation site has been reached, the lead members 202 may be moved into the deployed position. The distal portion 206 of each side lead member 212 is laterally spaced from the central lead member 210. In some embodiments, the distal portions 206 of the side lead members 212 are equally spaced from the distal portion 206 of the central lead member 210.

Figure 6:
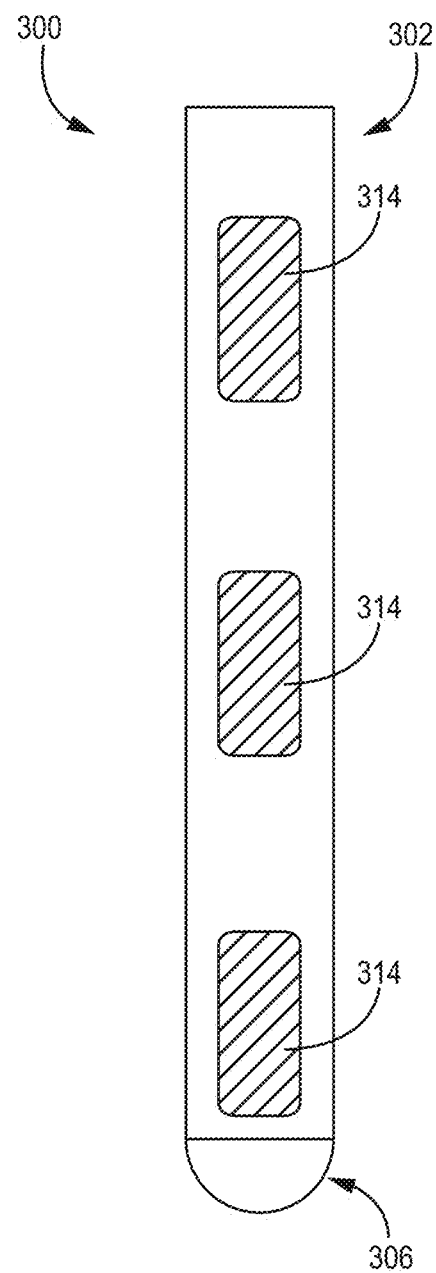
FIG. 6 is an elevation view of a lead member including electrodes.

FIG. 6 shows an elevation view of a lead member 302 of a lead assembly 300, which further illustrates the longitudinal spacing of the electrodes 314 on the lead member. Many of the parts and components depicted in FIG. 6 are the same or similar to those depicted in and described with regard to FIGS. 2 and 4. Reference is made to the discussion above regarding FIGS. 2 and 4 for numbered elements depicted in but not specifically discussed with regard to FIG. 6. The lead assembly 300 is similar to lead assemblies 100 and 200, and similar elements are numbered similarly (e.g., lead member 102 is similar to lead member 302).

The lead member 302 may include one or more discrete segments of electrodes 314. For example, each electrode 314 may not completely surround the lead member 302. For example, each lead member 302 can include more than one electrode 314 (e.g., electrode segment) spaced circumferentially around the lead member (e.g., inner and outer electrodes). Electrodes 314 on the lead number 302 may also be longitudinally spaced from the other electrodes on the lead member to facilitate longitudinal steering of an electrical field.

The lead member 302 may also have a smooth burrowing tip. For example, the tip may be rounded. In some embodiments, the distal portion 306 may be formed as a smooth burrowing tip. The smooth burrowing tip may be formed integrally with the lead member 302 or may be formed by attaching a rounded tab of the same or different material to the distal portion 306. The smooth burrowing tip may mitigate risks associated with lysing tissue during implantation, for example, as the lead member 302 extends from the deployable position to the deployed position.

Figure 7:
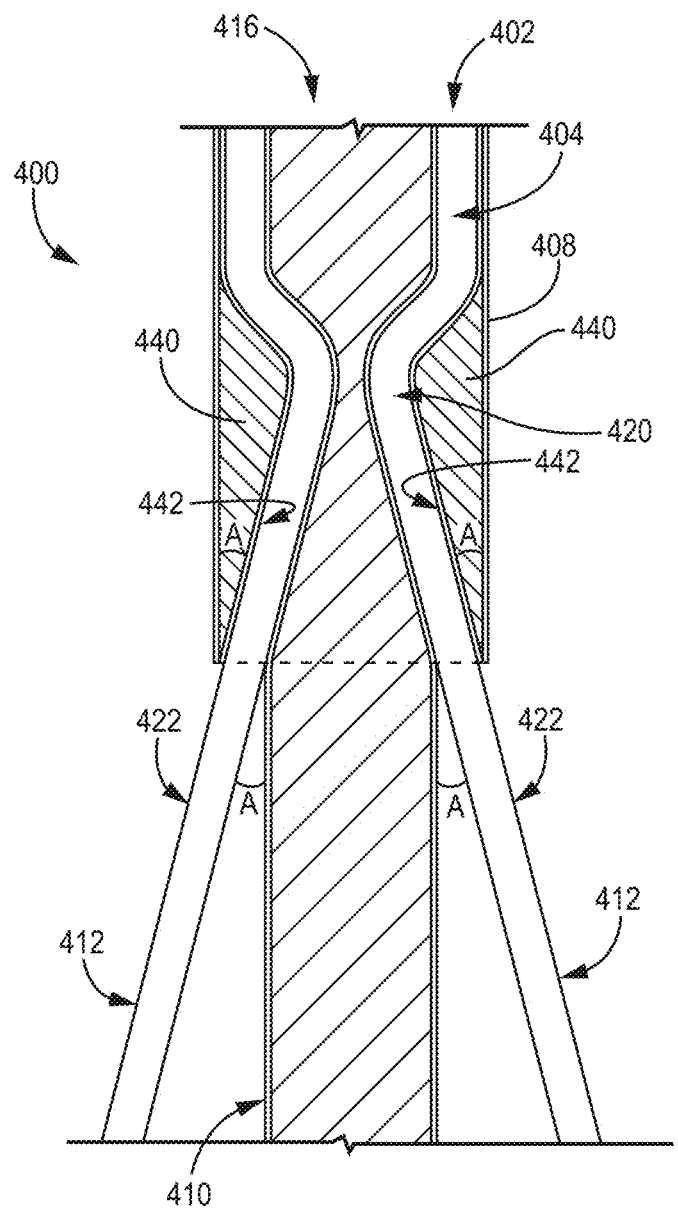
FIG. 7 is a schematic, partial elevation view of a lead assembly shown in a deployed position including a buckler.

FIG. 7 shows a schematic, partial elevation view of a lead assembly 400 in a deployed position including a buckler 440 to show more detail around a buckling point 420. Many of the parts and components depicted in FIG. 7 are the same or similar to those depicted in and described with regard to FIGS. 2, 4, and 6. Reference is made to the discussion above regarding FIGS. 2, 4, and 6 for numbered elements depicted in but not specifically discussed with regard to FIG. 7. The lead assembly 400 is similar to lead assemblies 100, 200, and 300, and similar elements are numbered similarly (e.g., lead member 102 is similar to lead member 402). The lead assembly 400 may also include electrodes (not shown) similar to electrodes 114, 214, and 314.

The lead assembly 400 may include one or more bucklers 440. In some embodiments, the lead assembly 400 includes one buckler 440 for each side lead member 412. In some embodiments, the lead assembly 400 includes one, two, three, four, or more bucklers 440. In the illustrated embodiment, two bucklers 440 are shown. The buckler 440 may be discretely formed or integrally formed with other bucklers 440 (e.g., integrally forming a ring).

The buckler 440 may be coupled to the cannula 408. In some embodiments, the buckler 440 is disposed in the lumen 416 of the cannula 408. In some embodiments, the buckler 440 is disposed at an end portion 418 of the cannula 408. The buckler 440 may be disposed adjacent to one or more side lead members 412 in the lumen 416.

Each buckler 440 may be configured to engage one or more side lead members 412. In some embodiments, the buckler 440 is adjacent a distal portion (not shown) of the side lead member 412 in the deployable position. In some embodiments, as the side lead member 412 extends out of the end portion 418 of the cannula 408, the buckler 440 engages the side lead member 412.

The buckler 440 may be sized and shaped to squeeze the lead members 402 such that the side lead member 412, or the stylet 450 (FIGS. 8A-E) coupled to the side lead member, is buckled into the central lead member 410 at a buckling point 420. The central lead member 410 may be resiliently deformable. The central lead member 410 may also be squeezed at the buckling point 420. The central lead member 410 may also include a lumen to accommodate a stylet (not shown) for deploying the central lead member 410.

The buckling point 420 may be defined at a point, line, or area where the side lead member 412 changes direction most drastically. The buckling point 420 may generally coincide with the location of engagement between the buckler 440 and the side lead member 412 or to the stylet 450 (FIGS. 8A-E) coupled to the side lead member. In some embodiments, the buckler 440 forms a deploying portion 422 in the side lead member 412 past the buckling point 420. In some embodiments, in the deployed position, the side lead member 412 may exhibit a bundled portion 404 and a deploying portion 422 extending from the distal portion 418 of the cannula 408.

In some embodiments, the buckler 440 is formed as a bump or protrusion extending inwardly from the cannula 408 into the lumen 416. The buckler 440 may taper in a distal part of the buckler 440.

A distal part of the buckler 440 may set an exit angle A for the side lead member 412. In some embodiments, the buckler 440 may include an exit surface 442 defining the exit angle A for the associated side lead member 412. The exit surface 442 may include a planar or almost planar surface. In some embodiments, the exit angle A is parallel to or almost parallel to the exit surface 442.

In some embodiments, the side lead member 412 may extend generally linearly within the cannula 408, and past the buckling point 420, the side lead member 412 may be redirected outwardly due to the spring back of the central lead member 410 pressing the side lead member 412 against the exit surface 442 defining the exit angle A. Beyond the exit surface 442, the deploying portion 422 may extend along a constant-radius arc, for example, when coupled to a stylet, such as stylet 450 (FIGS. 8A-E). The side lead member 412 may be generally flexible or semi-flexible in the lateral direction and be encouraged in the lateral direction to extend along a non-linear pathway defined by the stylet 450.

The exit angle A of the side lead member 412 may be defined with reference to the longitudinal axis, the direction of the lumen 416 of the cannula 408, or the direction of the central lead member 410, which may all extend along the same or similar lines. The exit angle A may be a maximum angle for the side lead member 412. The exit angle A may be selected based on balancing factors, such as a large enough angle to form a sufficient electrode array width for stimulation coverage and a small enough angle to facilitate safe explantation or extraction of the side lead member 412 (e.g., too large of an angle may increase risks associated with undesirably extracting tissue).

The exit angle A may be large enough to provide sufficient lateral field steering for the electrode array. In some embodiments, the exit angle A is greater than or equal to about 3 degrees, about 5 degrees, about 7 degrees, about 8 degrees, or about 9 degrees.

The exit angle A may be also shallow enough to provide safe explantation of the lead members 402. In some embodiments, the exit angle A is less than or equal to about 17 degrees, about 15 degrees, about 11 degrees, about 10 degrees, or about 9 degrees.

In some embodiments, the exit angle A ranges from about 5 degrees to about 15 degrees, about 7 degrees to about 11 degrees, about 8 degrees to about 10 degrees, or is equal to about 9 degrees.

The exit surface 442 may be a distal surface of the bump or protrusion. As the side lead member 412 moves out of the end portion 418 of the cannula 408, the side lead member 412 may engage with the exit surface 442 of the buckler 440 immediately before exiting the cannula 408.

The buckler 440 may engage a side of the side lead member 412. In some embodiments, the buckler 440 engages only one side of the side lead member 412. In some embodiments, the buckler 440 may also engage other sides of the side lead member 412.

The buckler 440 may not engage the central lead member 410. The central lead member 410 may not be deflected by the buckler 440 and may be free of a deflection portion or buckling point.

Figure 8A:
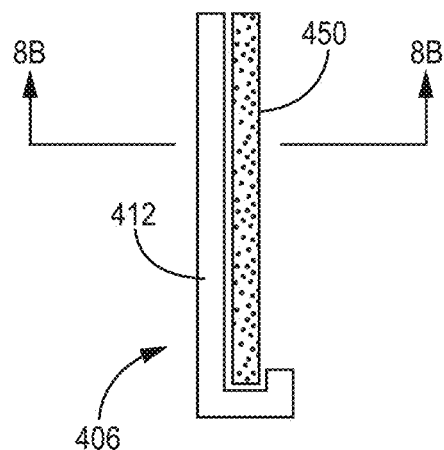
FIG. 8A is a schematic elevation view of the lead assembly of FIG. 7 and a stylet.

FIG. 8A shows a schematic elevation view of the lead assembly 400 and a stylet 450. For illustrative purposes, the side lead member 412 and the stylet 450 are shown extending substantially linearly, but the stylet 450 may extend along a non-linear pathway when unconstrained and define the non-linear pathway of the side lead member 412 when deployed. Also, for illustrative purposes, only the distal portion 406 of the side lead member is shown, but the stylet 450 may extend along the entire length of the side lead member 412 (e.g., from a bundled portion to the distal portion 406) or along some of the side lead member (e.g., along a deploying portion).

The stylet 450 may be coupled to one or more of the side lead members 412 to impart lateral forces upon the side lead member 412. The lateral forces of the stylet 450 may guide the side lead member 412 along a constant curvature pathway, such as a constant-radius arc, when unconstrained (e.g., in the deployed position). The stylet 450 may also be used to push the side lead member 412 in a longitudinal direction, for example, from the deployable position to the deployed position. The distal portion 406 of the side lead member 412 may include a hooked tab, fold, or bucket to catch the stylet 450 as it is pushed longitudinally.

Figure 8B:
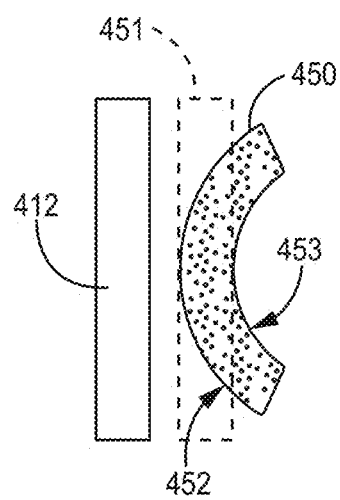
FIG. 8B is a schematic cross-sectional view of the lead assembly and stylet of FIG. 8A along line 8B-8B.

FIG. 8B shows a schematic cross-sectional view of the side lead member 412 and the stylet 450 along line 8B-8B shown in FIG. 8A. The stylet 450 may be formed of a super elastic material. The super elastic material may be capable of more than about 1%, about 2%, about 3%, about 4%, about 6%, about 8%, or about 10% elastic strain. The super elastic material may be a metal, such as nitinol. The stylet 450 may be formed into a shape that defines a non-linear pathway when unconstrained and also cooperatively engages a buckler, such as buckler 440 (FIG. 7), to be redirected outwardly in a lateral direction by the compression of the central lead member 410 (FIG. 7).

Figure 8D:
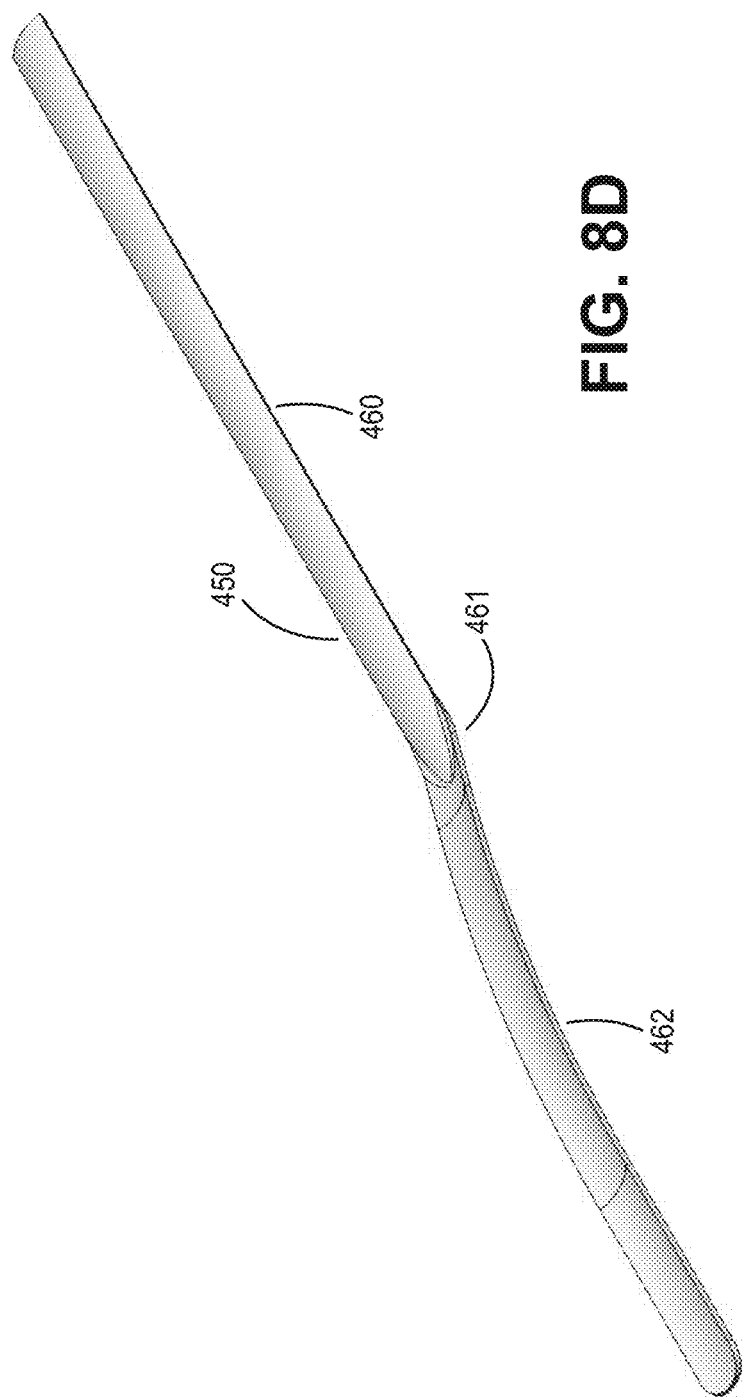
FIG. 8D is a perspective view of one of the deployment stylets of FIG. 8C.
Figure 8E:
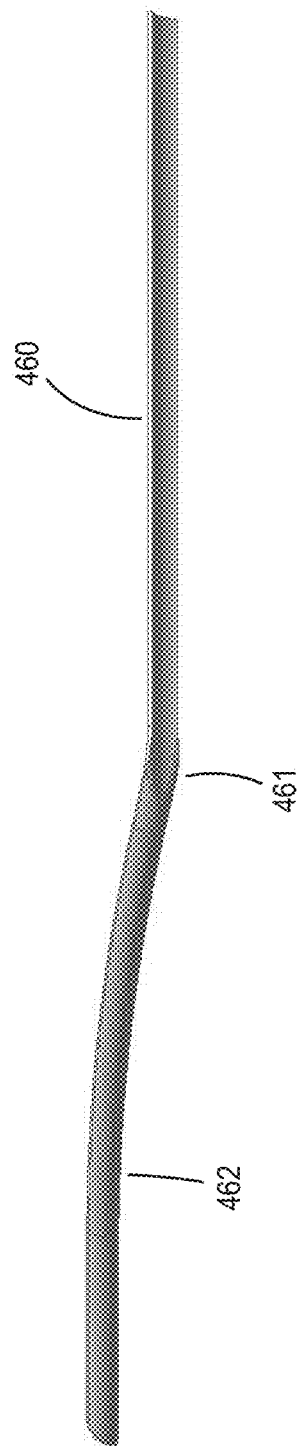
FIG. 8E is an elevation view of one of the deployment stylets of FIG. 8C.

FIGS. 8C-E show stylets 450 or a single stylet 450 as partially deployed with a section of the stylets 460 constrained within the delivery cannula, the buckled section 461, and the unconstrained portion 462 which is distal to the delivery cannula. FIG. 8C shows only the stylets 450 and the cannula. For clarity the lead sections are not shown. FIGS. 8D-8E are different views of a single stylet 450 from FIG. 8C with the cannula removed for clarity. In this embodiment shown in FIGS. 8C-E the stylets are shown curved to conform to the lead sections when the stylets are constrained within the cannula 460. The portion of the stylets outside of the cannula 462 which are unconstrained may exhibit a different cross section shape compared to the arcuate cross section shown for section 460 which is constrained by both the cannula and the lead sections.

In some embodiments, the stylet 450 has an arcuate cross-section when unconstrained. As the side lead member 412 and stylet 450 are pushed past the buckler, the buckler 450 buckles the stylet 450 to form a low flexural stiffness section of the stylet 461 that is locally flat. The buckling point 420 (FIG. 7) in the side lead member 412 may be formed adjacent to or at the same point the stylet 450 is buckled 461. For example, when the stylet 450 is unconstrained or not engaged by the buckler, the stylet 450 may have the arcuate cross-section. When the stylet 450 is engaged by the buckler, however, the stylet 450 takes on the shape of stylet 451 and flattens or is flatter than the unconstrained stylet 450. When flattened, the stylet 451 and 461 becomes flexible in the lateral direction and can conform to the exit angle A defined by the buckler. Because of the super elastic material, the shape of the stylet 451 may buckle and return to the arc shape of the stylet 450 upon passing the buckler and exiting the cannula.

In some embodiments, the stylet 450 may be disposed adjacent to the side lead member 412. In particular, the stylet 450 may have an exterior surface 452 of the arc adjacent to the side lead member 412. For example, the exterior surface 452 of the arc of the stylet 450 may be oriented toward the side lead member 412. The stylet 450 may be described as having an outward orientation relative to the side lead member 412. This orientation may facilitate the cooperation between the buckler and the stylet 450 to flare the side lead member 412 and stylet 450 outward (e.g., from the central lead member). When the stylet 450 is flattened, the stylet 450 will tend to bend toward an inner surface of the distal end of the cannula, for example, because of compression of the central lead member 410 pushing the stylet 450 and the side lead member 412 against the exit surface 442 (FIG. 7).

The edges of the stylet 450 may be rounded or include a rounded tab disposed on the edges of the arc to mitigate risks associated with lysing tissue during deployment as the side lead member 412 and stylet 450 are pushed through tissue.

In other embodiments (not shown), the inner surface 453 of the stylet 450 is adjacent to or oriented toward the side lead member 412, and the stylet 450 is disposed on the other side of the side lead member 412 (e.g., the stylet 450 is disposed closer to the central lead member than the side lead member 412). In this manner, when the stylet 450 is flattened, the stylet 450 will flare the side lead member 412 and stylet 450 outward (e.g., from the central lead member), because the stylet 450 tends to bend toward the inner surface 453 upon being flattened. This orientation may mitigate the need to have rounded edges of the stylet 450, as the edges would be oriented toward the side lead member 412 instead of tissue during deployment.

Figure 9:
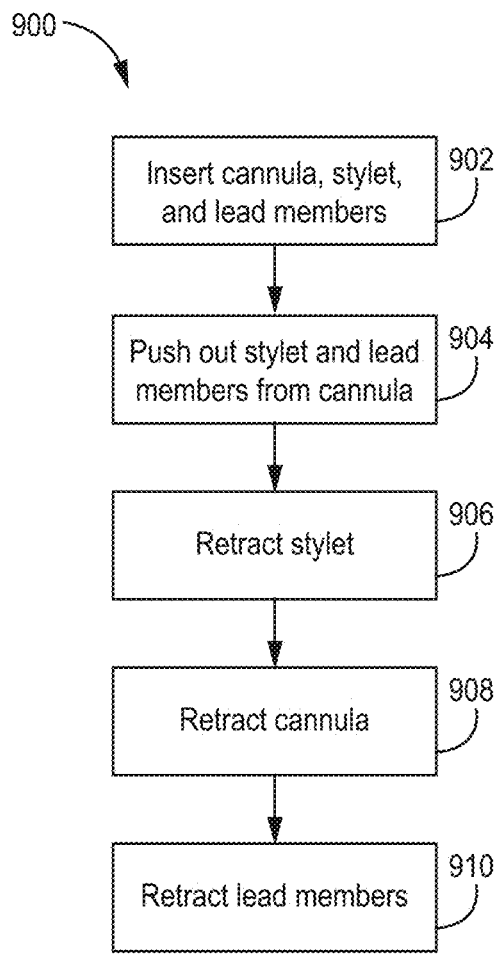
FIG. 9 is a schematic representation of a method of using any of the lead assemblies of FIG. 1, 4, 6, or 7.

FIG. 9 shows a schematic representation of a method 900 of using any of the lead assemblies 100, 200, 300, or 400. At step 902, a lead assembly including a cannula, stylets, and lead members with electrodes is inserted into the tissue of a patient in a deployable position and guided by a user toward an implantation site. The patient may be generally anesthetized or unconscious during implantation. Once the target implantation site is reached, the stylet may be pushed out of the end of the cannula, which also pushes one or more lead members out of the cannula and into a deployed position, at step 904. After step 904, the electrodes may be positioned at or adjacent to a target stimulation site.

With the electrodes implanted and deployed, the stylet may be retracted or removed from the tissue of the patient by the user in step 906. The cannula may then be retracted or removed from the tissue of the patient by the user in step 908, leaving the lead members with electrodes implanted in the tissue of the patient. With a sufficient range of electric field steering due to the physical configuration of the electrodes, stimulation therapy may be configured on a controller after the general anesthesia wears off the patient. Even after a substantial therapeutic period, the patient may wish to have the lead members with electrodes removed or repositioned for different therapeutic needs. Due to the small angle of the side lead members, the lead members may be safely extracted or removed from the tissue of the patient in step 910.

Thus, embodiments of the DEPLOYABLE ELECTRODE ARRAY LEAD ASSEMBLY FOR IMPLANTABLE ELECTRICAL STIMULATION are disclosed. Although reference is made to the accompanying set of drawings that form a part hereof and in which are shown by way of illustration several specific embodiments, it is to be understood that other embodiments are contemplated and may be made without departing from (e.g., still falling within) the scope or spirit of the present disclosure. The detailed description, therefore, is not to be taken in a limiting sense.

All references and publications cited herein are expressly incorporated herein by reference in their entirety into this disclosure, except to the extent they may directly contradict this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements).

Terms related to orientation, such as "proximal", "distal", "longitudinal", "lateral", "adjacent to", "side", "end", and other similar terms are used to describe relative positions of components and are not meant to limit the orientation of the embodiments contemplated. For example, an embodiment described as having a "proximal portion" and "distal portion" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The term "and/or" means one or all of the listed elements or a combination of any two or more of the listed elements (e.g., casting and/or treating an alloy means casting, treating, or both casting and treating the alloy).

The phrases "at least one of," "comprises at least one of," and "one or more of" followed by a list refers to any one of the items in the list and any combination of two or more items in the list.

What is claimed is:

1. A lead assembly comprising:
a central lead member comprising a distal portion configured to extend along a longitudinal axis;
two or more side lead members disposed around the central lead member, each side lead member comprising a deploying portion extending at an angle away from the longitudinal axis, each deploying portion having a proximal portion and a distal portion, the distal portion being laterally spaced from the central lead member and extending more parallel to the longitudinal axis than the proximal portion such that:
a tangent line to any point of the distal portion:
forms a distal acute angle with the longitudinal axis;
or is parallel to the longitudinal axis; and
a tangent line to any point of the proximal portion forms a proximal acute angle with the longitudinal axis that is greater than a magnitude of the distal acute angle and no greater than the angle away from the longitudinal axis,
each deploying portion of the side lead members extending along a constant-radius arc that is convex; and
one or more electrodes attached to the distal portion of the deploying portion of each side lead member.

2. The lead assembly according to claim 1, further comprising two or more electrodes attached to each deploying portion.

3. The lead assembly according to claim 2, wherein the electrodes form an electrode array having two or more longitudinally-spaced rows of electrodes.

4. The lead assembly according to claim 3, wherein the electrode array comprises three or more rows.

5. The lead assembly according to claim 3, wherein the electrode array comprises pairs of inner and outer electrodes.

6. The lead assembly according to claim 3, wherein the electrodes in each row have the same spatial configuration.

7. The lead assembly according to claim 6, wherein two or more electrodes are attached to a deploying portion of the central lead member and each row includes at least one electrode on the central lead member.

8. The lead assembly according to claim 6, wherein the diameter of the electrode array is greater than or equal to 3 mm.

9. The lead assembly according to claim 1, further comprising a stylet coupled to each of the side lead members configured to guide the side lead members along the constant-radius arc when deployed.

10. The lead assembly according to claim 9, wherein the stylet has an arcuate cross-section configured to be resiliently flattened by a buckler.

11. The lead assembly according to claim 10, wherein an exterior surface of the arcuate cross-section is oriented toward the side lead member.

12. The lead assembly according to claim 1, wherein each of the side lead members has a smooth burrowing tip.

13. The lead assembly according to claim 1, wherein the central lead member and the side lead members define a round cross section when within a lumen.

14. The lead assembly according to claim 13, wherein the round cross section defines a diameter less than or equal to 2.6 mm.

15. The lead assembly according to claim 1, wherein the side lead members comprise three or more side lead members.

16. The lead assembly according to claim 1, further comprising filars each coupled to a different one of the electrodes.

17. The lead assembly according to claim 1, wherein the electrodes are electrically coupled to a controller configured to steer an electrical field greater than or equal to 1.5 mm in the lateral direction from the central lead member.

18. The lead assembly according to claim 1, further comprising a hermetic multiplexer coupled to the electrodes.

19. A system comprising:
a stimulation device; and
a lead assembly according to claim 1.

20. The lead assembly according to claim 1, wherein the distal acute angle is no greater than 2 degrees and no less than -2 degrees.

* * * * *